US010617546B2

(12) United States Patent
Turrini et al.

(10) Patent No.: US 10,617,546 B2
(45) Date of Patent: Apr. 14, 2020

(54) MANUALLY OPERATED ROTATIVE LOCKING DEVICE FOR ORTHOPEDIC ORTHOSES OR BRACES

(71) Applicant: F.G.P. S.R.L., Verona (IT)

(72) Inventors: Alberto Turrini, Verona (IT); Moreno Ferrigolo, Verona (IT)

(73) Assignee: F.G.P. S.R.L., Verona (IT)

( * ) Notice: Subject to any disclaimer, the term of this patent is extended or adjusted under 35 U.S.C. 154(b) by 383 days.

(21) Appl. No.: 15/518,051

(22) PCT Filed: Dec. 22, 2015

(86) PCT No.: PCT/EP2015/080959
§ 371 (c)(1),
(2) Date: Apr. 10, 2017

(87) PCT Pub. No.: WO2016/134807
PCT Pub. Date: Sep. 1, 2016

(65) Prior Publication Data
US 2017/0304102 A1    Oct. 26, 2017

(30) Foreign Application Priority Data

Feb. 27, 2015    (IT) .............................. VR2015A0033

(51) Int. Cl.
*A61F 5/01*          (2006.01)
*A43C 11/16*         (2006.01)

(52) U.S. Cl.
CPC .............. *A61F 5/01* (2013.01); *A43C 11/165* (2013.01); *A61F 5/0111* (2013.01); *A61F 2005/0158* (2013.01)

(58) Field of Classification Search
CPC .. A61F 5/01; A61F 5/0111; A61F 2005/0158; A43C 11/165; A43C 11/00
See application file for complete search history.

(56) References Cited

U.S. PATENT DOCUMENTS

2007/0084956 A1    4/2007    Chen
2010/0139057 A1*   6/2010    Soderberg .............. A43C 11/16
                                                    24/68 R
(Continued)

FOREIGN PATENT DOCUMENTS

EP    0651954 A1    5/1995
EP    1213981 B1    9/2008
EP    2789251 A1    10/2014

OTHER PUBLICATIONS

Patent Cooperation Treaty, International Search Report and Written Opinion of the International Searching Authority for PCT/2015/080959, dated Mar. 11, 2016, 9 pages.

*Primary Examiner* — Tarla R Patel
(74) *Attorney, Agent, or Firm* — Heslin Rothenberg Farley & Mesiti P.C.; Stephen P. Scuderi

(57) ABSTRACT

A blocking device for fastening orthoses used in the orthopedic-rehabilitation sector to parts of the body of a person comprises a casing housing a cable wound on a reel by the rotation of a knob restrained to the casing during the winding stage and partially releasable from the casing by pushing and/or pulling the knob, in order to operate with respect to a ratchet-type non-return system, wherein the ratchet-type non-return system consists of elastic tabs which are part of the casing, and an inner toothed edge of the knob. The knob is restrained in a rotating direction and unrestrained in an axial direction with respect to the reel by a pin with a shaped head, whereby the restraint between the knob and the reel is achieved by a shaped axial opening in the knob, which reflects the shape of the head of the pin, wherein maintaining the knob in the gripping/release positions is ensured by the concave profiles present on the shaped head of the pin and convex surfaces present in the opening of the knob, thereby allowing the knob to be moved from a gripping condition with the ratchet-type non-return system in the tightening and (Continued)

blocking stage to a release condition in the opening stage while maintaining control of the cable wound on the reel.

10 Claims, 3 Drawing Sheets

(56) References Cited

U.S. PATENT DOCUMENTS

| | | | | |
|---|---|---|---|---|
| 2013/0092780 A1* | 4/2013 | Soderberg | ............ | A43C 11/165 |
| | | | | 242/396.4 |
| 2015/0007422 A1* | 1/2015 | Cavanagh | ............ | A43C 11/165 |
| | | | | 24/68 SK |
| 2017/0224056 A1* | 8/2017 | Midorikawa | .......... | A43B 23/02 |

* cited by examiner

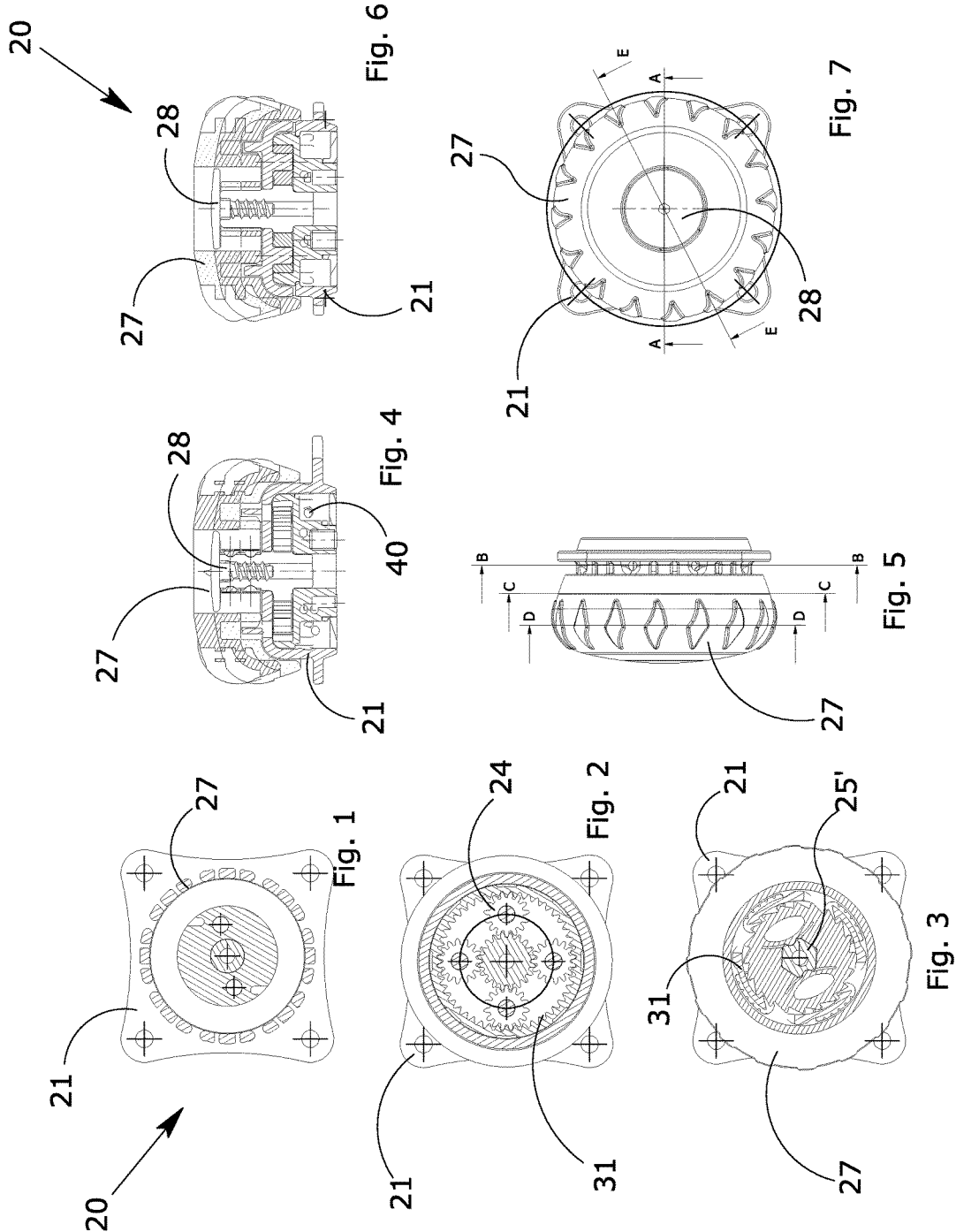

MANUALLY OPERATED ROTATIVE LOCKING DEVICE FOR ORTHOPEDIC ORTHOSES OR BRACES

CROSS REFERENCE TO RELATED APPLICATIONS

This application is a National Stage filing under section 371 of International Application No. PCT/EP2015/080959, filed on Dec. 22, 2015, and published on Sep. 1, 2016, as WO 2016/134807 A1 and claims priority to Italian Application No. VR2015A000033, filed on Feb. 27, 2015. The entire disclosures of each of the prior applications are hereby incorporated herein by reference.

TECHNICAL FIELD

The present invention concerns a device for locking by means of fastening for applications in the orthopedic-rehabilitation sector, usable by means of a rotatably operated knob system.

The locking device according to the invention can be used in the orthopedic sector, to lock and/or close the flaps of orthoses and/or braces that must be kept in a certain position.

With respect to known solutions, the locking device according to the invention proposes that the locking knob, which acts on a reel that winds the constraint cable, can control the fastening in a very precise and functional way, perfecting in particular both the locking steps, with fine adjustment, and the release steps which can be controlled with greater precision compared to traditional rotatably operated locking systems.

BACKGROUND ART

The use of fastening or locking means operated by a rotatable knob has been known for some time for many applications, currently mainly in the footwear sector, consisting of a casing that is attached to a first flap of the item to be locked, for example a shoe or boot, a knob with a reel rotatably attached to the casing, at least one cable attached at one end to a reel around which it is wound and at the other end, on the exterior of the casing, to a second flap of the item to be locked.

By way of example, fastening means of this type, specifically concerning the footwear sector, are described in documents EP 1213981 B1 and EP 2789251 A1.

By operating the knob it is possible to rotate the reel which, by winding the cable, causes the two flaps attached to the ends of the cable to move closer together in order to achieve a correct degree of locking.

The rotatable knob is therefore positioned on the exterior of the casing and is designed to cause the rotation of the reel by manual control, to tighten the locking cable. In addition, the knob and the reel can be axially released from each other so that the knob can be moved from a gripping position with the reel to a release position in which the cable is unwound from the reel, releasing the fastening.

Mechanical means, designed to block the reel in the desired position in one rotation direction and designed to release the reel in the opposite direction, are present between the knob and the reel.

These mechanical means consist of gear mechanisms that interact, in the locking step, with the means of constraint, generally the ratchet type, with which the reel is provided, and operate in such a way that the knob can be moved from a lowered gripping position, in which the cable is tautened and locked, and rotated to a raised release position to allow the release and slackening of the cable.

The problem encountered with the use of such devices substantially concerns the fact that in the release step, allowed by raising the knob which frees the reel, the cable unwinds in an uncontrolled and instantaneous way, immediately releasing the previously constrained parts, since the knob is normally constrained to the reel only in the gripping step, while it is completely freed from the reel which becomes idle in the release step with the knob raised.

The uncontrolled opening due to the instantaneous release of the cable when the knob is raised from the gripping position could, in some situations, cause problems, especially in cases in which this type of fastening is used in combination with some particular applications, such as orthoses or braces used in the orthopedic and rehabilitation sector, in which conditions of instantaneous release, starting from a restraining or gripping position, could lead to the immediate detachment of components that should, instead, preferably, and in some cases necessarily, open gradually.

Document US 2007/0084956 A1 discloses a string fastening device including a reel on which a string is reeled thereon and a toothed ring is connected to the reel. A knob has a shaft inserted into a tube extending from the base of the device and the reel is rotatably mounted on the tube. The knob has first teeth in an underside thereof and the first teeth are engaged with the toothed ring so that the reel is driven by rotation of the knob to tighten the ring. The knob can be pulled away from the reel to disengage the first teeth from the toothed ring so that the string can be loosened. The knob includes second teeth and the base has two pawls which limit the knob to rotate in one direction to drive the reel.

DESCRIPTION OF THE INVENTION

The present invention proposes to provide a locking device for the orthopedic-rehabilitation sector that can be used by means of a rotatably operated knob system which is controlled at least during the release step, in order to eliminate or at least reduce the drawbacks described above.

The invention proposes in particular to provide a locking device by means of a rotatably operated knob system that foresees the use of means designed to control the release, making it possible to obtain gradual opening conditions for the release of orthopedic-rehabilitation type components, whose opening must necessarily be controlled in order to prevent excessively abrupt releases.

This is achieved by means of a rotatably operated locking device whose features are described in the main claim.

The dependent claims of the solution according to this invention describe advantageous embodiments of the invention.

The invention proposes a rotational system for the fastening of corrective or post-operative orthoses on the body, wherein the knob is connected to a reel on which to wind the cable by means of a reduction system or by direct drive and wherein this connection allows the knob to slide longitudinally along its axis, but does not allow it to rotate independently of the reel, permitting the knob to move from the "restrained" position to the "free" position, but under controlled release.

DESCRIPTION OF THE DRAWINGS

Other features and advantages of the invention will become clear on reading the description given below of one embodiment, provided as a non-limiting example, with the help of the accompanying drawings, in which:

FIGS. 1 to 3 represent schematic horizontal cross-section views of various levels of the locking device by means of the rotatably operated system according to the invention, according to the respective cross-section lines B-B, C-C, D-D, of FIG. 5;

FIG. 4 is a schematic cross section view of the rotation device in the raised opening position, according to the plane defined by the line E-E of FIG. 7, with finer lines showing the knob in the gripping position;

FIG. 5 is a schematic side view of the locking device according to the invention;

FIG. 6 is a schematic cross section view of the locking device in the gripping position with the knob lowered, according to the plane defined by the line A-A of FIG. 7, with finer lines showing the knob in the release position;

FIG. 7 shows the locking device according to the invention in plan view;

DESCRIPTION OF A FORM OF EMBODIMENT OF THE INVENTION

Figures 8, 9:
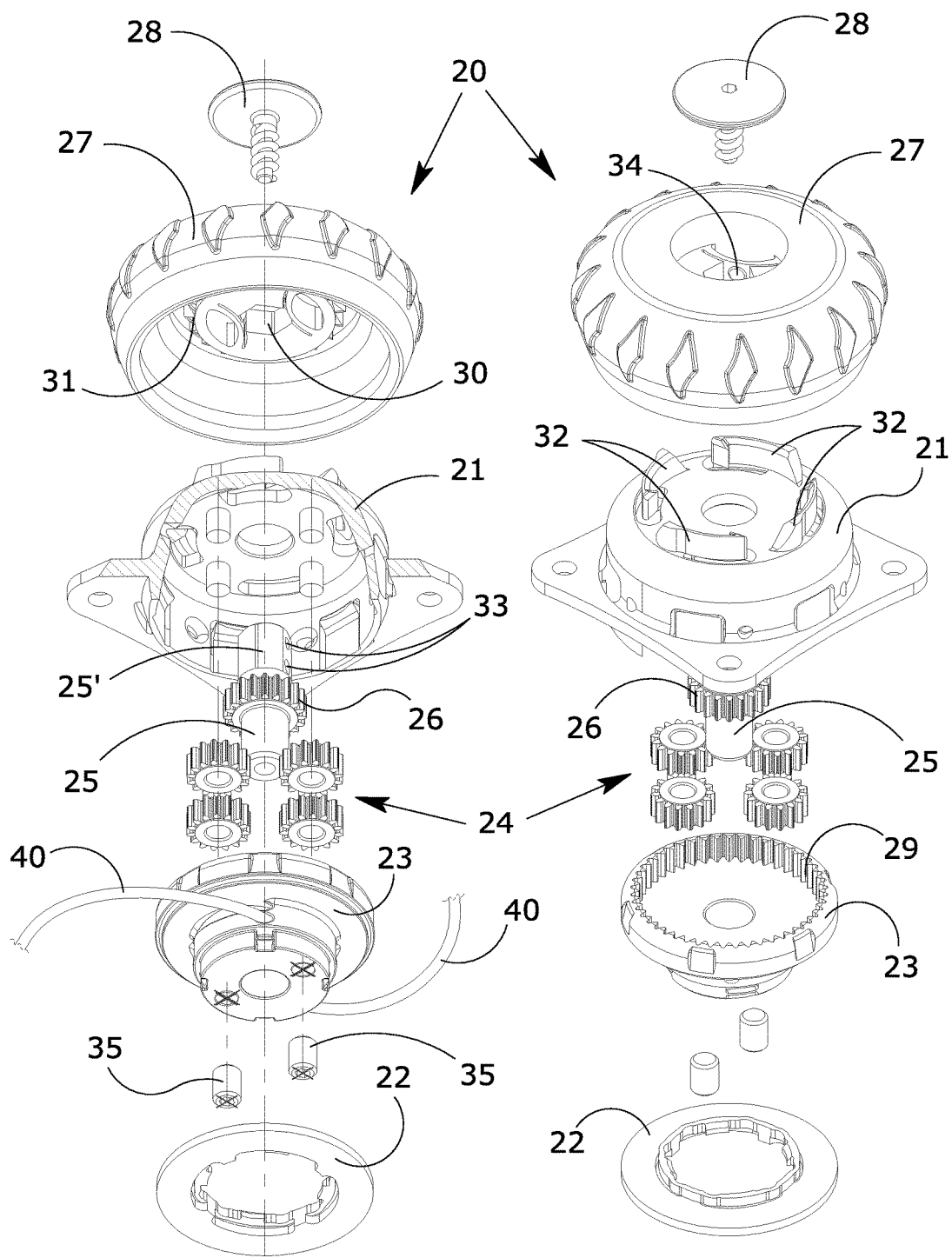
FIG. 8 is a schematic exploded view showing the components of the locking device from the bottom upwards.
FIG. 9 is a schematic exploded view showing the components of the locking device from the top downwards.
Figure 10:
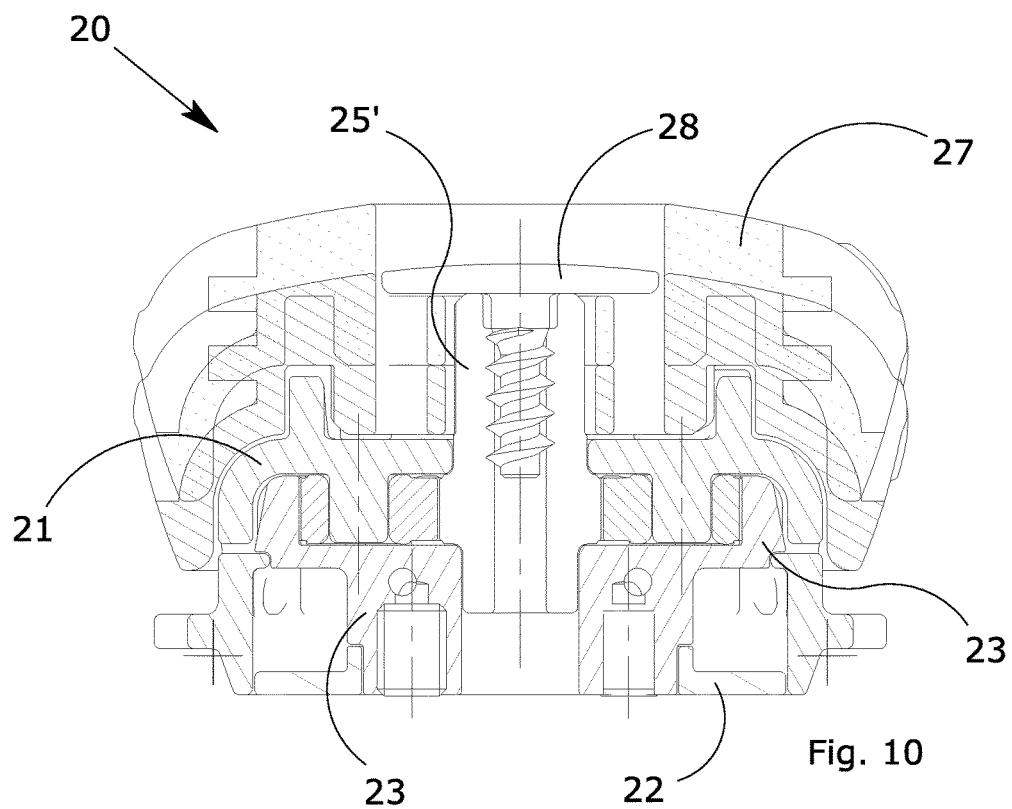
FIG. 10 shows a schematic cross-section view of the locking device on the vertical central plane, with the knob in the lowered gripping position, with finer lines showing the knob in the release position.

With reference to FIGS. 8 and 9, reference sign 20 denotes in its entirety a locking device according to the invention.

As can be seen in FIG. 8, the locking device 20 comprises a series of components contained inside a casing 21, consisting from the bottom upwards of a lower retaining ring 22, a reel 23, a set of reduction gears 24, and a pin with a shaped head 25, equipped with a toothed ring nut 26 that can be used with reduction gears.

According to other embodiments (not shown in the figures), the set of reduction gears 24 and the toothed ring nut 26 are not present.

A fastening cable 40 is wound around the reel 23 and is held in position on the reel by means of the lower restraining ring 22 and blocked from slipping off the reel by means of screw elements 35 (FIG. 8).

On the outside of the casing 21 is a knob 27 which can be fixed to the shaped head 25' protruding from the pin 25 by means of a screw 28.

As shown in FIGS. 8 and 9, in which the reduction gears 24 are used, particularly in the case of precision use, the reel 23 comprises an upper cavity whose inner edge is provided with toothing 29 designed to engage with the reduction gears 24.

The restraint between the knob 27 and the reel is obtained by a shaped axial opening 30 in the knob which respects the shaping of the head 25' of the pin 25, thus allowing rotational restraint with the simultaneous possibility of axial sliding of the knob with respect to the reel.

In addition, the knob 27 has a lower cavity whose inner border is provided with a toothed edge 31 engaging with four-sector circular elastic tabs 32 with flexible toothed ends; the toothed edge 31 and the elastic tabs 32 constitute a ratchet which allows the knob 27 to be rotated in one direction only.

The connection between the knob 27 and the reel 23 allows the knob to slide longitudinally to its axis, but does not allow it to rotate independently of the reel 23, thereby maintaining the axial restraint.

The movement along its axis thus allows the knob 27 to switch from the "gripping" position to the "free" position with respect to the ratchet 31-32, but maintaining a rotational restraint between the knob and the reel.

The reel 23 is connected to the knob 27 by means of a reduction system, in this case epicycloidal, which allows greater precision during the screwing down and closing of the fastening, even if direct drive without reduction gears is foreseen.

The knob shifts from one position to the other by means of pushing down during the gripping step and pulling upwards along its axis in the release step, and is held in the selected position by means of the ratchet system, which constitutes an elastic system that allows the knob to couple in a semi-stable way with the reel (for the system that functions with direct drive).

A screw 28, or other equivalent system, prevents the knob 27 from uncoupling from the pin 25, acting as a stop in the raised opening step, preventing it from exceeding the limit of the ratchet release position.

Figure 11:
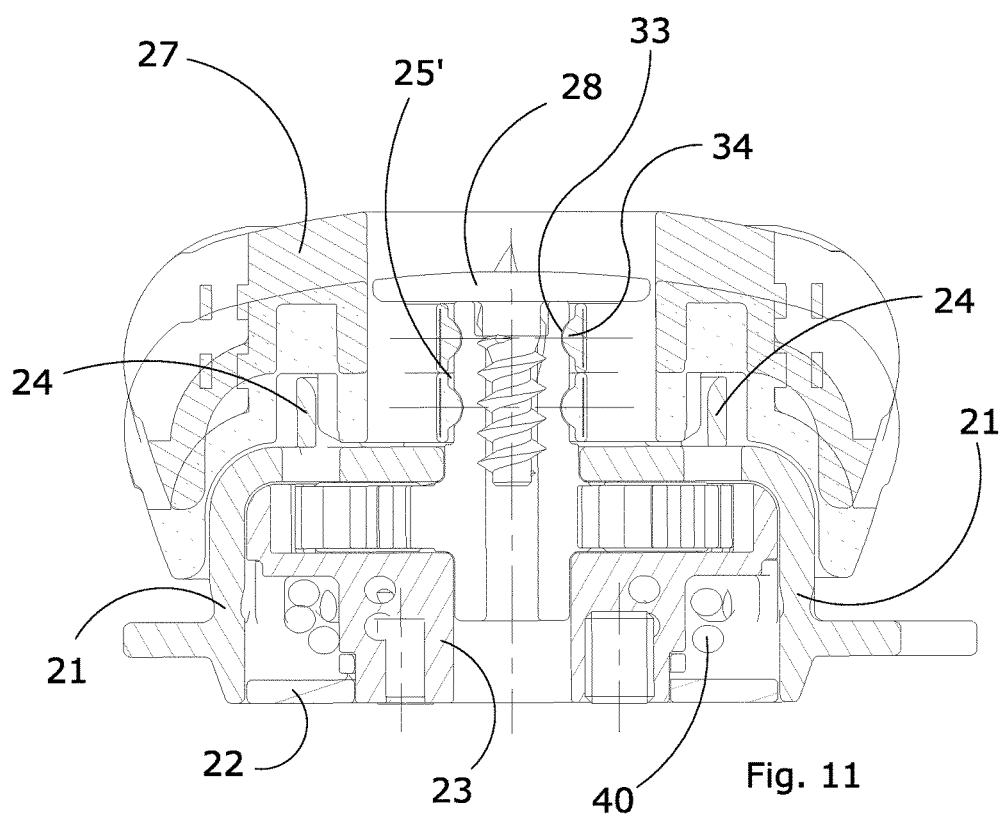
FIG. 11 is a schematic cross-section view of the locking device on the vertical central plane, with the knob in the raised release position, with finer lines showing the knob in the gripping position.

As can be seen in FIG. 11, maintaining the knob 27 in the gripping/release positions is guaranteed by the interface between the concave profiles 33 present on one segment 25' of the pin 25 and the corresponding convex surfaces 34 present in the cavity 30 of the knob 27. Thanks to their intrinsic elasticity, these convex surfaces 34 allow the knob 27 to shift from the gripping position to the release position (and vice versa) and to maintain the selected position, with the necessary stability.

In the gripping position, the knob can be turned to wind in the cable, but cannot be turned in the opposite direction to release the cable as it is restrained by the flexible teeth forming part of the casing 21, being positioned on its inner ring-like edge.

In orthopedic applications, the casing 21 is fixed on a part of the orthosis and the cable 40 partially wound onto the reel is used as a connecting element to a second part of the orthosis.

When the knob 27 is turned to the gripping position, the cable is tautened and the two parts connected to the ends of the cable are brought together, while when the knob is released from the teeth 32 of the casing by pulling it upwards, the two parts of the orthosis can be moved apart, freeing these parts of the orthosis which were restrained on the body of the person.

The invention as described above refers to a preferred embodiment. It is nevertheless clear that the invention is susceptible to numerous variations falling within the scope of the disclosure, in the context of technical equivalents.

The invention claimed is:

1. A locking device for fastening orthoses used in the orthopedic-rehabilitation sector and configured to use for parts of a body of a person, the device comprising a casing housing a cable wound on a reel by the rotation of a knob restrained to the casing during the winding stage and partially releasable from the casing by pushing and/or pulling the knob, in order to operate with respect to a ratchet-type non-return system, wherein the ratchet-type non-return system comprises elastic tabs which are part of the casing, and an inner toothed edge of the knob, wherein the knob is restrained in a rotating direction and unrestrained in an axial direction with respect to the reel by a pin with a shaped head, whereby restraint between the knob and the reel is achieved by a shaped axial opening in the knob, which reflects a shape of the head of the pin, the shaped axial opening enabling the knob to slide axially along the shaped head from a gripping position to a release position, wherein maintaining the knob in the gripping/release positions is ensured by at least a first and a second concave profile present on the shaped head of the pin and at least a convex surface present in an opening of the knob, wherein, when the knob is in the gripping position, the convex surface is positioned to engage the first concave profile to maintain the knob in the gripping position and, when the knob is in the release position, the convex surface is positioned to engage the second concave profile to maintain the knob in the release position, thereby allowing the knob to be removed from the gripping position with the ratchet-type non-return system in the tightening and blocking stage to the release position in the opening stage while maintaining control of the cable wound on the reel.

2. A locking device according to claim 1, wherein the casing houses a lower grommet and the reel on which the cable is wound.

3. A locking device according to claim 2, wherein the casing also encloses a gear unit, in that the pin is equipped with a toothed ring nut engaging with the gear unit, and in that the real comprises an upper cavity with a toothed inner edge designed to engage with the gears of the gear unit.

4. A locking device according to claim 2, wherein the knob is positioned outside the casing and is only restrained rotatably, while it can slide axially, to the shaped head protruding from the pin, by means of a screw.

5. A locking device according to claim 4, wherein the casing also encloses a gear unit, whereby the pin is equipped with a toothed ring nut engaging with the gear unit, and whereby the real comprises an upper cavity with a toothed inner edge designed to engage with the gears of the gear unit.

6. A locking device according to claim 5, wherein the restraint between the knob and the reel is obtained by a shaped axial opening in the knob which respects the shaping of the head of the pin, thus allowing rotational restraint with the simultaneous possibility of axial sliding of the knob with respect to the reel.

7. A locking device according to claim 6, wherein the connection between the knob and the reel allows the knob to slide longitudinally to its axis, but does not allow it to rotate independently of a reel, thereby maintaining the radial restraint.

8. A locking device according to claim 1, wherein the knob is positioned outside the casing and is only restrained rotatably, while it can slide axially, to the shaped head protruding from the pin, by means of a screw.

9. A locking device according to claim 1, wherein the restraint between the knob and the reel allows rotational restraint with the simultaneous possibility of axial sliding of the knob with respect to the reel.

10. A locking device according to claim 1, wherein the connection between the knob and the reel allows the knob to slide longitudinally to its axis, but does not allow it to rotate independently of the reel, thereby maintaining the radial restraint.

* * * * *